(12) United States Patent
Park et al.

(10) Patent No.: US 11,204,343 B2
(45) Date of Patent: Dec. 21, 2021

(54) METHOD FOR DETERMINING WHETHER OR NOT INFECTION WITH BURSAPHELENCHUS XYLOPHILUS

(71) Applicant: ECONNBIZ CO., LTD., Sejong-si (KR)

(72) Inventors: Yong Chan Park, Goyang-si (KR); Seong Bean Park, Suwon-si (KR)

(73) Assignee: ECONNBIZ CO., LTD., Sejong-si (KR)

( * ) Notice: Subject to any disclaimer, the term of this patent is extended or adjusted under 35 U.S.C. 154(b) by 259 days.

(21) Appl. No.: 16/692,681

(22) Filed: Nov. 22, 2019

(65) Prior Publication Data

US 2020/0088698 A1  Mar. 19, 2020

Related U.S. Application Data

(63) Continuation of application No. PCT/KR2018/015325, filed on Dec. 5, 2018.

(30) Foreign Application Priority Data

Dec. 20, 2017 (KR) .................. 10-2017-0175934

(51) Int. Cl.
*G01N 30/72* (2006.01)
*G01N 30/86* (2006.01)
*G01N 33/00* (2006.01)

(52) U.S. Cl.
CPC ..... *G01N 30/7206* (2013.01); *G01N 30/8675* (2013.01); *G01N 33/0098* (2013.01)

(58) Field of Classification Search
None
See application file for complete search history.

(56) References Cited

U.S. PATENT DOCUMENTS

| | | | | |
|---|---|---|---|---|
| 4,886,671 A | * | 12/1989 | Cryer .................. | A01N 37/02 424/641 |
| 2010/0047176 A1 | * | 2/2010 | Ravn .................. | G01N 33/5014 424/9.2 |

FOREIGN PATENT DOCUMENTS

KR  10-1805981 B1  11/2017

OTHER PUBLICATIONS

Isidorov, V.A. et al., "Gas Chromatographic-Mass Spectrometric Investigation of Metabolites From The Needles and Roots of Pine Seedlings at Early Stages of Pathogenic Fungi Armillaria Ostoyae Attack", Trees, vol. 22, No. 4, Feb. 2008, pp. 531-542.*
International Search Report issued in PCT/KR2018/015325; dated May 29, 2019.

(Continued)

*Primary Examiner* — Daniel S Larkin
(74) *Attorney, Agent, or Firm* — Studebaker & Brackett PC

(57) ABSTRACT

Provided is a method for determining whether or not infection with *Bursaphelenchus xylophilus* exists. The method includes a first sap extraction step of immersing a first fragment sample taken from a first tree in a solvent to extract a first sap contained in the first fragment sample of the first tree, a first concentration analysis step of analyzing a first concentration of an organic compound contained in the first sap, and a first comparison step of comparing the first concentration with a reference concentration of the organic compound contained in the sap of a tree that has not been infected with *Bursaphelenchus xylophilus*, so as to determine whether or not a coniferous tree is infected with *Bursaphelenchus xylophilus*.

13 Claims, 7 Drawing Sheets

(56) References Cited

OTHER PUBLICATIONS

Office Action issued in KR 10-2017-0175934; mailed by the Korean Intellectual Property Office dated Mar. 5, 2019.
Yuko Takeuchi et al.; "Volatile Compounds in Pine Stands Suffering From Pine Wilt Disease: Qualitative and Quantitative Evaluation"; Nematology; 2006; pp. 869-879; vol. 8, No. 6.
Li Lin Zhao et al.; "Chemotaxis of the Pinewood Nematode, *Bursaphelenchus xylophilus*, to Volatiles Associated with Host Pine, *Pinus massoniana*, and its Vector Monochamus alternatus"; Journal of Chemical Ecology; 2007; pp. 1207-1216; vol. 33.
Ji Eun Yun et al.; "Rapid Diagnosis of the Infection of Pine Tree with Pine Wood Nematode (*Bursaphelenchus xylophilus*) by Use of Host-Tree Volatiles"; Journal of Agricultural and Food Chemistry; 2012; pp. 7392-7397; vol. 60.

\* cited by examiner

| No. | RT (min) | Match (%) | Compound Name | M.W. | Formula | Area |
|---|---|---|---|---|---|---|
| 1 | 7.531 | 99 | ALPHA.-PINENE,(-)- | 136 | C10H16 | 4706406 |
| 2 | 9.62 | 93 | Dodecane,2,6,10-trimethyl- | 212 | C15H32 | 464096 |
| 3 | 12.135 | 90 | (+)-(1R,5R)-2(10)-PINEN-4-ONE | 150 | C10H14O | 653255 |
| 4 | 13.049 | 93 | Dodecane,2,6,11-trimethyl- | 212 | C15H32 | 407874 |
| 5 | 15.927 | 90 | Eicosane | 282 | C20H42 | 1245274 |
| 6 | 18.472 | 90 | Eicosane | 282 | C20H42 | 1455439 |
| 7 | 19.492 | 95 | 1-Octadecene | 253 | C18H36 | 1656559 |
| 8 | 20.156 | 65 | Cholest-22-ene-21-ol, 3,5-dehydro-6-methoxy-, pivalate | 498 | C33H54O3 | 1460986 |
| 9 | 20.740 | 58 | Dotriacontane | 450 | C32H66 | 3084235 |
| 10 | 21.197 | 83 | Octadecanoic acid | 284 | C18H36O2 | 1636443 |
| 11 | 21.584 | 92 | 1-Hexacosene | 364 | C26H52 | 556439 |
| 12 | 23.414 | 90 | 9-Octadecenal,(Z)- | 266 | C18H34O | 5501841 |
| 13 | 23.743 | 84 | 2-7-Hexadecenal | 238 | C16H30O | 1741375 |
| 14 | 24.26 | 91 | 9-Tricosene,(Z)- | 322 | C23H46 | 3790116 |
| 15 | 25.757 | 69 | 1-Heptatriacotanol | 536 | C37H76O | 1412719 |
| 16 | 27.698 | 63 | 9-Octadecenamide,(Z)- | 281 | C18H35NO | 4246863 |

FIG. 8

| No. | RT (min) | Match (%) | Compound Name | M.W. | Formula | Area |
|---|---|---|---|---|---|---|
| 1 | 7.533 | 99 | .ALPHA.-PINENE,(-)- | 136 | C10H16 | 9487874 |
| 2 | 8.349 | 97 | 2-.BETA.-PINENE | 136 | C10H16 | 417609 |
| 3 | 9.622 | 92 | Dodecane,2,6,10-trimethyl- | 212 | C15H32 | 665834 |
| 4 | 11.159 | 93 | Verbenol | 152 | C10H16O | 1460769 |
| 5 | 11.659 | 73 | 9-Octadecen-12-ynoicacid,methylester | 292 | C19H32O2 | 480607 |
| 6 | 12.194 | 85 | (+)-(1R,5R)-2(10)-PIPEN-4-ONE | 150 | C10H14O | 575319 |
| 7 | 13.044 | 93 | Dodecane,2,6,11-trimethyl- | 212 | C15H32 | 497674 |
| 8 | 14.288 | 83 | .alpha.-Longipinene | 204 | C15H24 | 1018205 |
| 9 | 15.138 | 96 | Junipene | 204 | C15H24 | 13475555 |
| 10 | 15.927 | 91 | Eicosane | 282 | C20H42 | 1736300 |
| 11 | 17.583 | 90 | Longiborneol | 222 | C15H26O | 801465 |
| 12 | 18.487 | 96 | Eicosane | 282 | C20H42 | 1806095 |
| 13 | 19.49 | 96 | 1-Octadecene | 252 | C18H36 | 2187423 |
| 14 | 20.182 | 65 | Cholest-20-ene-(1-a), 3,5-dehydro-6-methoxy-, pivalate | 493 | C33H54O3 | 917519 |
| 15 | 20.746 | 90 | Dotriacontane | 450 | C32H66 | 1659538 |
| 16 | 23.411 | 99 | cis-Vaccenic acid | 282 | C18H34O2 | 8876811 |
| 17 | 24.288 | 87 | Kauran-18-al,17-(acetyloxy)-,(4.beta.)- | 346 | C22H34O3 | 6143010 |
| 18 | 25.228 | 83 | Kauran-18-al,17-(acetyloxy)-,(4.beta.)- | 346 | C22H34O3 | 4286184 |
| 19 | 25.759 | 65 | Silenene | 272 | C20H32 | 4846749 |
| 20 | 26.697 | 81 | Kaur-16-en-19-ol | 288 | C20H32O | 2980012 |
| 21 | 27.312 | 87 | Hexadecanoic acid, 4-nitrophenyl ester | 377 | C22H35NO4 | 1802759 |
| 22 | 27.716 | 85 | 9-Octadecenamide,(Z)- | 281 | C18H35NO | 4739042 |

FIG. 9

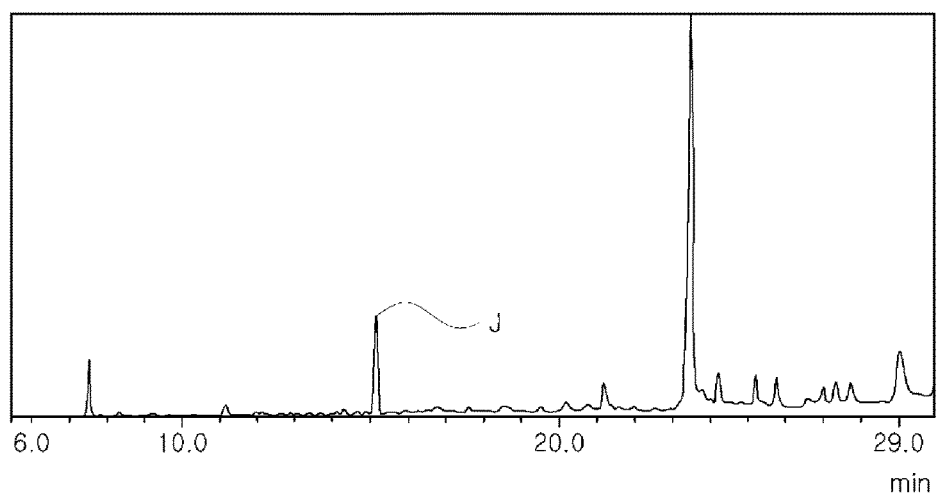

METHOD FOR DETERMINING WHETHER OR NOT INFECTION WITH BURSAPHELENCHUS XYLOPHILUS

CROSS-REFERENCE TO RELATED APPLICATIONS

The present application is a continuation of International Patent Application No. PCT/KR2018/015325, filed Dec. 5, 2018, which is based upon and claims the benefit of priority to Korean Patent Application No. 10-2017-0175934 filed on Dec. 20, 2017. The disclosures of the above-listed applications are hereby incorporated by reference herein in their entirety.

BACKGROUND

Embodiments of the inventive concept described herein relate to a method for determining whether a coniferous tree is infected with *Bursaphelenchus xylophilus*, which includes taking a fragment of the tree, extracting a sap from the taken fragment, analyzing the extracted sap to determine whether the tree is infected with *Bursaphelenchus xylophilus*.

Many kinds of pathogens and pests inhabit soil and plants and include phytoparasites known to affect plant growth inhibition and onset of disease directly or indirectly. Among the phytoparasites, *Bursaphelenchus xylophilus* taxonomically belongs to genus *Bursaphelenchus, Parasitaphelenchidae, Aphelenchida*, and 49 species have been reported around the world (Easy Pine wilt disease, National Institute of Forest Science, 2005). In addition, *Bursaphelenchus xylophilus* is a nematode of about 1 mm in size, thread-shaped, a harmful nematode, which blocks a movement path of moisture and nutrients in tree tissue and causes the tree to die. Because the *Bursaphelenchus xylophilus* do not have an ability to move itself to other pines, the *Bursaphelenchus xylophilus* travels through an insect vector, *Monochamus alternatus*, and a latent insect vector, *Monochanus saltuarius*, to infect other healthy pines. Larvae and chrysalis of *Monochanus saltuarius* grow in the pine. When *Monochanus saltuarius* emerges to escape from the tree, *Monochanus saltuarius* retains *Bursaphelenchus xylophilus* in a body. When an adult of emerging *Monochanus saltuarius* nibbles away one or two-year new shoot (when maturation feeding), the pine is infected with *Bursaphelenchus xylophilus*. The infected pine usually falls off on the $6^{th}$ day, leaves begin to wither from the $20^{th}$ day, and the leaves rapidly turn red after 30 days to die within a year.

Meanwhile, pine wilt disease caused by *Bursaphelenchus xylophilus* occurs in all part of the world, such as Asia including Japan, the United States, the Americas, Europe. In a case of Japan, since 1941, pines and black pines covering an area of 240 million m3 per year have withered to be nearly destroyed. In China, since the pine wilt disease first broke out in Nanjing City in 1982, it has severely damaged Chinese red pine (*Pinus massoniana* Lambert) and black pine forest. In Taiwan, since the pine wilt disease first broke out in 1985, a special species, Luchu pine (*Pinus Luchuensis*) is in danger of extinction. In addition, in Korea, since the pines began to be infected with *Bursaphelenchus xylophilus* in 1988, the pine wilt disease has occurred in 53 cities and continued to spread throughout the country. Therefore, there are environmental problems to cause huge economic losses.

SUMMARY

The inventors of the inventive concept believe that early determination of infection to be controlled rapidly based on the determination is the best ways to prevent pine wilt disease because there is a fear that coniferous trees are extinct due to pine wilt disease. Accordingly, the present inventors recognizes that it is an urgent problem to quickly determine whether pine coniferous trees are infected with pine wilt disease and have completed the inventive concept.

Embodiments of the inventive concept provide a method for analyzing sap components extracted form a coniferous tree and determining whether the tree is infected with pine wilt disease.

Other objects and advantages of the inventive concept will become apparent from the following detailed description, claims and drawings.

According to an exemplary embodiment, a method for determining whether a coniferous tree is infected with *Bursaphelenchus xylophilus* or not, the method includes performing a first sap extraction including immersing a first fragment sample taken from a first tree in a solvent and extracting a first sap of the first tree contained in the first fragment sample, performing a first analysis where a first concentration of an organic compound contained in the first sap is analyzed, and performing a first comparison where the first concentration is compared with a reference concentration of an organic compound contained in a sap of a tree uninfected with *Bursaphelenchus xylophilus*.

In addition, the performing of the first sap extraction may include immersing the first fragment sample in the solvent for 0.5 to 2 hours, and a mixture ratio of the first fragment sample and the solvent is 1:1 to 1:3 by mass.

In addition, the solvent may be selected from one or more of acetone, ethyl acetate, diethyl ether, glycerin, ethylene glycol, propylene glycol, butylene glycol, benzene, chloroform, hexane, and alcohol having 1 to 4 carbon atoms.

In addition, the method may further include determining the first tree is infected with *Bursaphelenchus xylophilus* or not depending on a result of the performing of the first comparison, wherein, when at least one of a first condition where a concentration of junipene contained in the first concentration is higher than a concentration of junipene contained in the reference concentration or a second condition where a concentration of (Z)-9-octadekenamide contained in the first concentration is higher than a concentration of (Z)-9-octadekenamide contained in the reference concentration is satisfied, the first tree may be determined to be an infected tree.

In addition, the method may further include calculating a first inspection distance based on the concentration of junipene or a concentration value of (Z)-9-octadekenamide contained in the first concentration when the first tree is determined to be an uninfected tree, performing a second sap extraction including immersing a second fragment sample taken from at least one second tree located within the first inspection distance and extracting a second sap of the second tree contained in the second fragment sample, performing a second analysis where a second concentration of an organic compound contained in the second sap is analyzed, and performing a second comparison where the second concentration is compared with the reference concentration or the first concentration.

In addition, the method may further include performing a second determination where pines located within the first inspection distance are determined to be uninfected tree when a concentration of junipene or a concentration of (Z)-9-octadekenamide contained in the second concentration is lower than the concentration of junipene or the concentration of (Z)-9-octadekenamide contained in the reference concentration or when the concentration of junipene or the concentration of (Z)-9-octadekenamide contained in the second concentration is lower than a critical ratio of the first concentration.

In addition, the method may further include calculating a second inspection distance based on the concentration of junipene or a concentration value of (Z)-9-octadekenamide contained in the first concentration when the first tree is determined to be an infected tree, performing a third sap extraction including immersing a third fragment sample taken from at least one third tree located within the second inspection distance in the solvent and extracting a third sap of the third tree contained in the third fragment sample, performing a third analysis where a third concentration of an organic compound contained in the third sap is analyzed, and performing a third comparison where the third concentration is compared with the reference concentration or the first concentration.

In addition, the method may further include performing a third determination where pines located within the second inspection distance are determined to be infected trees when a concentration of junipene or a concentration of (Z)-9-octadekenamide contained in the third concentration is higher than the reference concentration.

In addition, the method may further include determining the third tree as an uninfected tree when the concentration of junipene contained or the concentration value of (Z)-9-octadekenamide contained in the third concentration is lower than the concentration of junipene or the concentration of (Z)-9-octadekenamide contained in the reference concentration and calculating a third inspection distance from the third tree based on the concentration of junipene contained in the third concentration or the concentration value of (Z)-9-octadekenamide contained in the third concentration.

In addition, the method may further include performing a fourth sap extraction including immersing a fourth fragment sample taken from the first tree after a specific time from when the first fragment is taken, when the first tree is determined to be an uninfected tree in the first determination and extracting a fourth sap of the first tree contained in the fourth fragment sample, performing a fourth analysis where the fourth concentration of an organic compound of the fourth sap is analyzed, and setting the first tree to a protective monitoring tree when at least one of the concentration of junipene or the concentration of (Z)-9-octadekenamide contained in the fourth concentration rises more than the critical ratio of the concentration contained in the first concentration.

In addition, the method may further include introducing the extracted sap into a gas chromatograph mass spectrometer and obtaining a chart containing an organic compound of the sap.

In addition, the coniferous tree may be any one of pine (*Pinus densiflora*), Korean pine (*Pinus koraiensis*), black pine (*Pinus thunbergii*), Japanese white pine (*Pinus parviflora*), white pine (*Pinus strobus*), pitch pine (*Pinus rigida*).

In addition, the pine may any one of Japanese larch (*Larix kaempferi*), spruce (*Picea jezoensis*), needle fir (*Abies holophylla*), Himalayan cedar (*Cedrus deodara*).

Pine wilt disease infection determination program according to another embodiment of the inventive concept is combined with a computer which is hardware to execute the above-described the method for determining whether or not infection with *Bursaphelenchus xylophilus*, which are stored on medium.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 8 is a table illustrating concentrations of organic compounds of FIG. 7 in detail;

FIGS. 9 and 10 are diagrams illustrating organic compound peaks of a sap of a wild pine.

DETAILED DESCRIPTION

Figure 1:
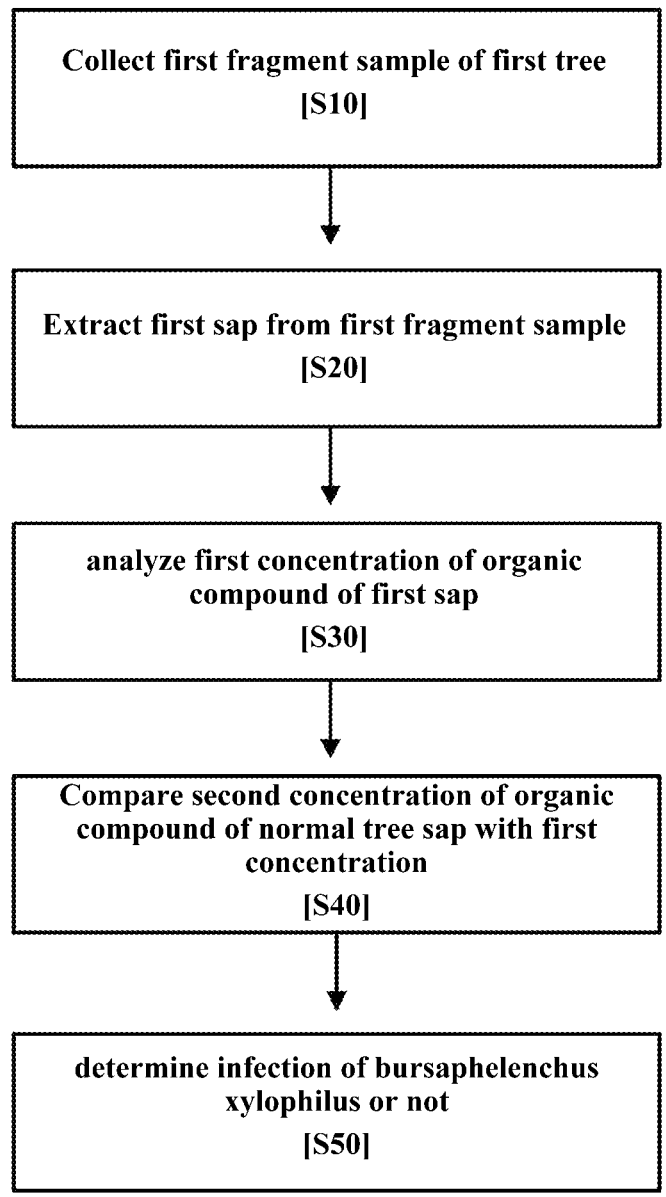
FIG. 1 is a flowchart of a method for determining whether a coniferous tree is infected with *Bursaphelenchus xylophilus* or not according to an embodiment of the inventive concept.

The advantages and features of the inventive concept and a method for achieving the same will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept and the inventive concept is only defined by the scope of the claims, The same reference numerals denote the same elements throughout the specification. Hereinafter, exemplary embodiments of the present invention will be described in detail with reference to the accompanying drawings. Regardless of the drawings, the same reference numbers refer to the same components, and "and/or" includes each and every combination of one or more of the items mentioned.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Hereinafter, a method for determining whether a coniferous tree is infected with *Bursaphelenchus xylophilus* or not according to an embodiment of the inventive concept will be described.

The inventive concept quickly determines whether a wild coniferous tree is infected with pine wilt disease or not. The pine wilt disease is referred to as a necrosis of pine by a nematode. Here, the coniferous tree includes any one of pine (*Pinus densiflora*), Korean pine (*Pinus koraiensis*), black pine (*Pinus thunbergii*), Japanese white pine (*Pinus parviflora*), and white pine (*Pinus strobus*). In addition, the pine is any one of Japanese larch (*Larix kaempferi*), Spruce (*Picea jezoensis*), Needle fir (*Abies holophylla*), and Himalayan cedar (*Cedrus deodara*). Namely, according to the inventive concept, it may be easy to determine whether the above-described coniferous tree is infected with *Bursaphelenchus xylophilus* or not.

*Bursaphelenchus xylophilus* is a nematode which nibbles away a tree while being parasitic in the pine and the Korean pine. *Bursaphelenchus xylophilus* is a small nematode as a female is 0.7 to 1.0 mm in length and a male is 0.6 to 0.8 mm in length. *Bursaphelenchus xylophilus* and *Monochamus alternatus* have a symbiotic relationship. *Bursaphelenchus xylophilus* in *Monochamus alternatus* is invaded into a tree tissue by *Monochamus alternatus*, initially inhabits xylem and cortical resin tube, and eats parenchyma cells of the pine to survive. Furthermore, *Bursaphelenchus xylophilus* survives about 35 days at room temperature and is known to develop into an imago via a larval stage including four instars (1st to 4th). *Bursaphelenchus xylophilus* is known for proliferative power because time required for the first generation is about 6 days at 25° C. and one pair multiplies to 200,000 after 20 days.

However, the pine infected with *Bursaphelenchus xylophilus* is caused by necrosis of parenchyma cells surrounding the resin tube and a passage of moisture and nutrients is blocked to wither away. Once the tree is infected with *Bursaphelenchus xylophilus*, the nearly 100% trees withers away, and thus the pine wilt disease is called "pine AIDS disease". Because a natural enemy of *Monochamus alternatus* which is an insect vector of *Bursaphelenchus xylophilus* is not to practical use, infection of the pine with *Bursaphelenchus xylophilus* is very dangerous to lead to extinction of massive pine forests.

Meanwhile, *Bursaphelenchus xylophilus* includes "dispersed *Bursaphelenchus xylophilus*" and "proliferative *Bursaphelenchus xylophilus*". "Dispersed *Bursaphelenchus xylophilus*" is referred that *Bursaphelenchus xylophilus* enters in a tissue of a healthy pine through a wounded area which occurs when the insect vector bites and eats the healthy pine to spread and to be infected after continuously breeding in the xylem of the pine, transforming into a dispersive third larva in February to May to gather around a pupal cell of *Monochamus alternatus*, the insect vector of *Bursaphelenchus xylophilus*, transforming into a dispersive fourth larva to invade an imago of the insect vector. "Proliferative *Bursaphelenchus xylophilus*" is a form of continuous proliferation in the infected pine throughout its lifetime as the dispersive fourth larva enters the healthy pine, turns into an adult to lay eggs, and transforms the eggs into a first larva, a second larva, a third larva, a fourth larva, and an adult, not to be a dispersive form. Actually, the pine dies due to Proliferative *Bursaphelenchus xylophilus*.

Korea has tried early to prevent invasion of *Bursaphelenchus xylophilus*, which has been designated as a prohibited pest under the Plant Protection Act. Until now, various methods have been developed to control pine wilt disease. Among them, there are methods, such as a logging fumigation method, a logging incineration method, a logging crushing method, an insecticide spraying method, and a method of using a natural enemy.

The logging fumigation method is a method of cutting off dead trees infected with *Bursaphelenchus xylophilus* to extinct insect vectors by fumigation. However, because the fumigation may harm people and livestock, care should be taken when using the fumigation and especially, contact with eyes, nose, mouth and skin should be avoided. The logging incineration method involves cutting off dead trees infected with *Bursaphelenchus xylophilus* and stacking cut trees in a large open area and then burning stacked trees or burning cut trees using a portable incinerator. Although there is a definite effect on the removal of pests, there is a problem that a control period is extremely limited because of forest fires. The logging crushing method includes cutting off dead trees infected with *Bursaphelenchus xylophilus* and crushing the cut trees to a size of 1.5 cm or less using a wood chipper or a chipper to extinct larvae of the insect vectors in xylem. There is no environmental pollution and this method is low in forest fires because the dead trees are not accumulated in the forest. However, it is easy to drop the tree containing the insect vectors during transportation to crush the infected tree and it takes a lot of manpower and control costs. The insecticide spraying method may be controlled before maturation feeding of the pine by the insect vectors to prevent pine wilt disease, and therefore may prevent spread of damage and may be applied to large areas of forest. However, it is possible to destroy an ecosystem by killing beneficial insects and resistance of the pests may be increased to be necessary to develop additional insecticides. The insecticide spraying method is not a fundamental control method in terms of the effect. In addition, the method of using the natural enemy is an eco-friendly control means to maintain the food chain by restoring the ecosystem and includes an introduced natural enemy use method, a multiplication natural enemy use method, a natural enemy protection method, etc. However, there is a disadvantage that the control effect is inadequate.

Therefore, in order to effectively control *Bursaphelenchus xylophilus*, dead cause of pine may be quickly diagnosed to prevent death of pine from *Bursaphelenchus xylophilus* or control efficiency for *Bursaphelenchus xylophilus* may be increased to essentially control *Bursaphelenchus xylophilus*.

Accordingly, in the inventive concept, a sap may be extracted based on a sample of a fragment of wild coniferous tree and concentrations of substances contained in the sap may be analyzed to rapidly determine the sampled coniferous tree is infected with *Bursaphelenchus xylophilus* or not.

FIG. 1 is a flowchart of a method for determining whether a coniferous tree is infected with *Bursaphelenchus xylophilus* or not according to an embodiment of the inventive concept.

The inventive concept will be described with reference to FIG. 1. Hereinafter, for convenience of explanation, it is assumed that a coniferous tree is, for example, pine. That is, the pine indicated below is just described as an example for convenience of description, and it is possible to determine whether any of coniferous trees is infected with *Bursaphelenchus xylophilus* or not according to the following description.

In addition, in an embodiment of the inventive concept described below, a first tree 110, a second tree 120, and a third tree 130 mean wild coniferous trees, respectively. For convenience of description, the first tree 110, the second tree 120, and the third tree 130 are called as abridged forms.

In addition, in an embodiment of the inventive concept, a subject is a computer, more specifically, may be a determination server of whether or not infection of *Bursaphelenchus* xylophilus or a determination device of whether or not infection of *Bursaphelenchus xylophilus*.

Referring to FIG. 1, a first fragment sample is taken from the first tree 110 in S10.

In an embodiment of the inventive concept, a fragment sample of tree may be taken by a following method.

The wild pine may be punched using a drill and fragments of the wild pine may be separated in a process of punching. The separated fragments are collected to take the fragment sample of wild pine.

After S10, the first fragment sample taken from the first tree 110 is immersed in a solvent to extract a first sap of the first tree 110 contained in the first fragment sample in S20.

Here, in the first sap extraction in S20, a mixing ratio of the first fragment sample and the solvent is 1:1 to 1.3 by mass and the first fragment is immersed in the solvent for 0.5 to 2 hours.

In an embodiment of the inventive concept, when all saps are extracted, the mixing ratio of the fragment sample and the solvent is 1:1 to 1.3 by mass and the first fragment is immersed in the solvent for 0.5 to 2 hours.

When a mass of the solvent is less than a mass of the fragment sample, the extraction of the sap contained in the fragment sample may not be performed smoothly. Meanwhile, when the mass of the solvent is more than three times over the mass of the fragment sample, extraction effect of more than three times does not appear, and thus unnecessary costs increase with increasing solvent use, which is uneconomical.

The fragment sample may be immersed in the solvent at room temperature to perform the extraction for 0.5 hours to 2 hours. When the immersion time is less than 0.5 hours, the sap of pine may not be extracted sufficiently. When the immersion time exceeds 2 hours, it may not be possible to rapidly determine whether the pine is infected with *Bursaphelenchus xylophilus* or not.

The solvent may be used for the sap extraction. The solvent may be selected from one or more of acetone, ethyl acetate, diethyl ether, glycerin, ethylene glycol, propylene glycol, butylene glycol, benzene, chloroform, hexane, and alcohol having 1 to 4 carbon atoms.

After S20, a first concentration of an organic compound contained in the first sap is analyzed in S30.

For example, a gas chromatograph mass spectrometer (GC-MS) may be used. That is, the extracted sap is introduced into the gas chromatograph mass spectrometer and the first concentration of the organic compound contained in the sap is measured. Here, the first concentration may be calculated based on a peak of the organic compound shown in the gas chromatograph mass spectrometer.

Meanwhile, the organic compound contained in the sap is as follows. That is, the organic compound contained in the sap includes:

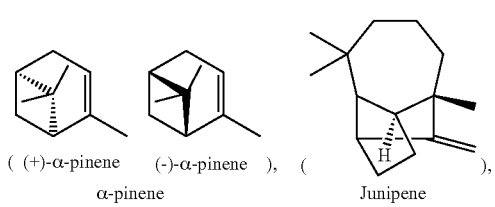

( (+)-α-pinene    (-)-α-pinene ),   (       ),
       α-pinene                    Junipene

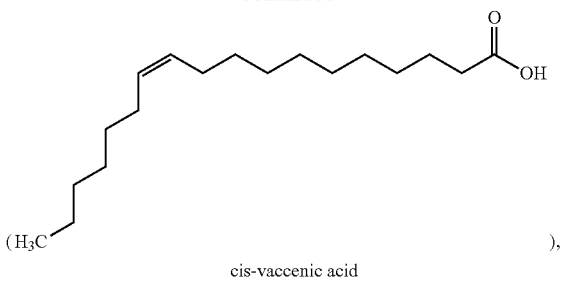

cis-vaccenic acid

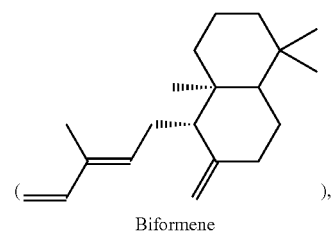

Biformene

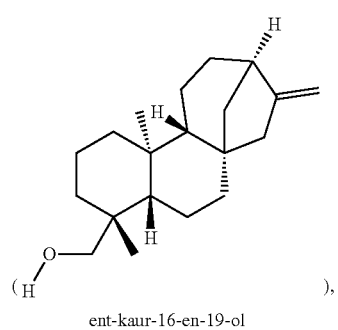

ent-kaur-16-en-19-ol

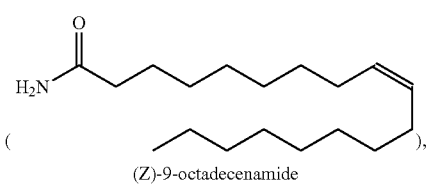

(Z)-9-octadecenamide

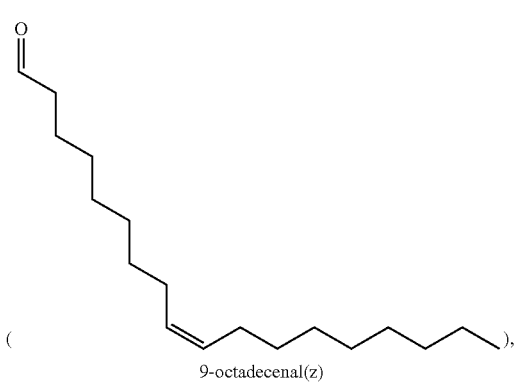

9-octadecenal(z)

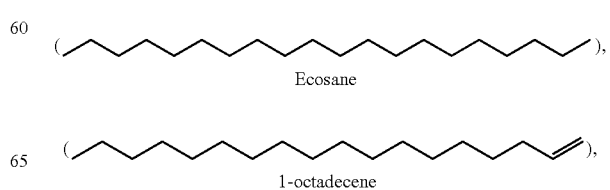

Ecosane 1-octadecene

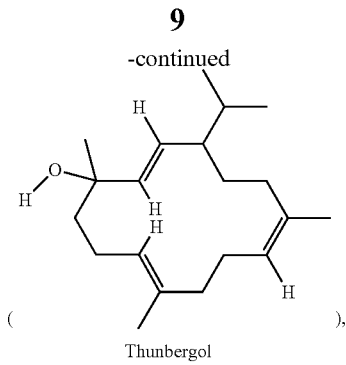

Thunbergol and so on.

Among these, an organic compound found in a normal tree, which is not infected with *Bursaphelenchus xylophilus*, is thunbergol.

Meanwhile, the organic compounds found in the infected tree with *Bursaphelenchus xylophilus* are biformene, ent-Kaur-16-en-19-ol, (Z)-9-octadekenamide, 9-octadecenal(z).

Meanwhile, substances having a higher concentration of the organic compound contained in the infected tree than the normal tree are α-pinene, junipene, ecosane, 1-octadecene.

A substance having a lower concentration of the organic compound contained in the infected tree than the normal tree is cis-Vaccenic acid.

The first concentration of the organic compound of the first sap extracted from the first fragment sample of the first tree 110 is compared with a reference concentration of the organic compound contained in the sap of the pine uninfected with *Bursaphelenchus xylophilus* in S40.

Here, the reference concentration is referred to as a concentration of the organic compound contained in the sap of the pine uninfected with *Bursaphelenchus xylophilus*.

Namely, the uninfected pine is the normal tree and the reference concentration of the organic compound of the normal tree may be used as a reference.

The sap is extracted from the uninfected pine and the concentration of components of the organic compound contained in the sap is set to the reference concentration.

Thereby, the first concentration of the organic compound contained in the sap randomly extracted from the first tree 110, which is the wild pine is compared with the reference concentration of the organic compound contained in the sap of the normal tree to determine whether the wild pine is infected with *Bursaphelenchus xylophilus*.

More specifically, when the first concentration of a specific organic compound and the reference concentration of the specific organic compound are different from each other, the wild tree is determined to be infected with *Bursaphelenchus xylophilus*.

In more detail, for example, the method may further include determining whether the first tree 110 is infected with *Bursaphelenchus xylophilus* or not based on a result of a first comparison in S50.

In detail, the method further includes a first determination. When at least one of a first condition where a concentration of junipene contained in the first concentration is higher than a concentration of junipene contained in the reference concentration and a second condition where a concentration of (Z)-9-octadekenamide contained in the first concentration is higher than a concentration of (Z)-9-octadekenamide contained in the reference concentration is satisfied, the first tree 110 is determined to be an infected tree.

Hereinafter, the inventive concept will be described in more detail with reference to Examples. These examples are only for illustrating the inventive concept in more detail and it will be apparent to those skilled in the art that the scope of the inventive concept is not limited by Examples in accordance with the gist of the inventive concept.

Experimental Example 1: Extraction of Sap from Normal and Infected Trees 100 g of a normal pine sample uninfected with *Bursaphelenchus xylophilus* and 100 g of an infected pine sample with *Bursaphelenchus xylophilus* were taken. Each sample taken was washed to remove foreign matter in each sample. After washing, each sample was dried in shade. Each dried sample was immersed in an organic solvent for 1 hour at room temperature (25° C.). 200 g of hexane was used as the organic solvent. After immersing, a sap of normal tree and a sap of infected tree were obtained by 10 g, respectively.

Experimental Example 2: Comparison of Gas Chromatograph Mass Spectrometer of Sap Extracted from Normal Tree and Sap Extracted from Infected Tree 3 g of sap of normal tree and 3 g of sap of infected tree, which were obtained in Experimental Example 1, were introduced into a gas chromatograph mass spectrometer (GC-MS) to obtain charts of organic compounds contained in the saps. The organic compound chart of the normal sap was shown in FIG. 2 and the organic compound chart of the infected sap was shown in FIG. 3.

Figure 2:
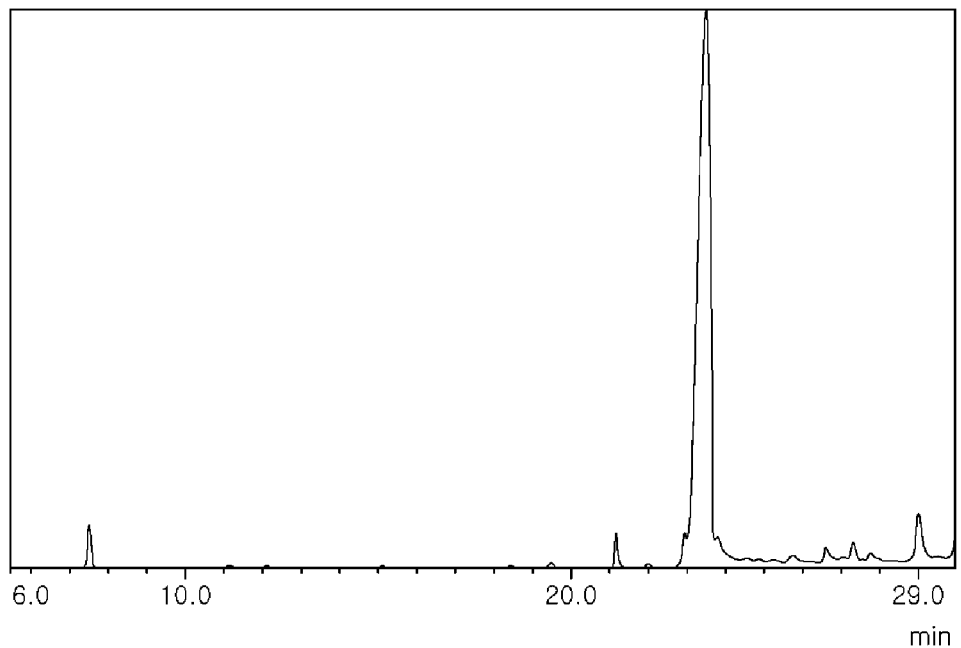
FIG. 2 is a diagram illustrating an organic compound chart of a sap of a normal tree.
Figure 3:
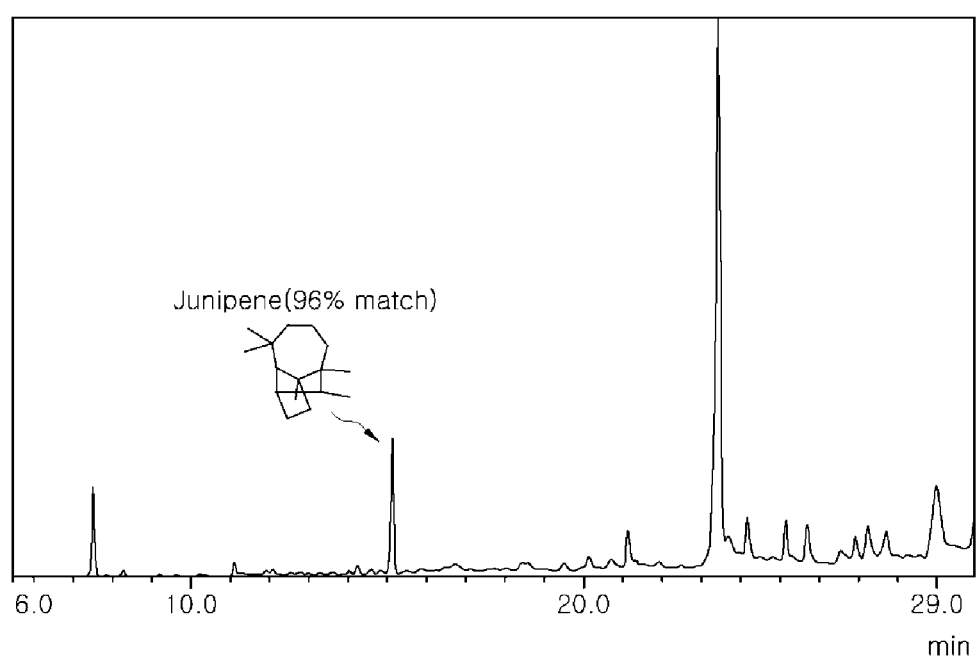
FIG. 3 is a diagram illustrating an organic compound chart of a sap of an infected tree.

FIG. 2 is a diagram illustrating an organic compound chart of a sap of a normal tree and FIG. 3 is a diagram illustrating an organic compound chart of a sap of an infected tree.

Referring to FIGS. 2 and 3, it was found that a concentration of an organic compound contained in sap of a normal tree and a concentration of an organic compound contained in sap of an infected tree differed in a specific portion.

More specifically, in FIG. 2 (the normal tree), a peak of junipene appeared to be weak, but in FIG. 3 (the infected tree) a peak of junipene appeared to be strong. As a result, it was found that a concentration of junipene in the infected tree was significantly higher than that of the normal tree.

Figure 4:
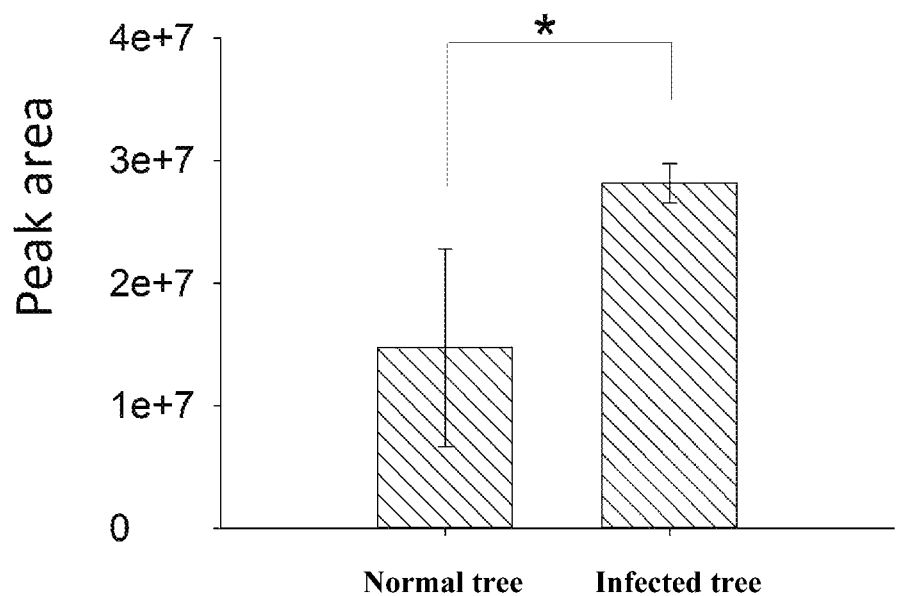
FIG. 4 is a diagram comparing junipene concentrations of a normal tree and an infected tree.

FIG. 4 is a diagram comparing junipene concentrations of a normal tree and an infected tree. As illustrated in FIG. 4, it was found the junipene concentration of the infected tree became high. In detail, the tree having a peak area of $2.3*10^7$ or more was determined to be an infected tree.

Figure 5:
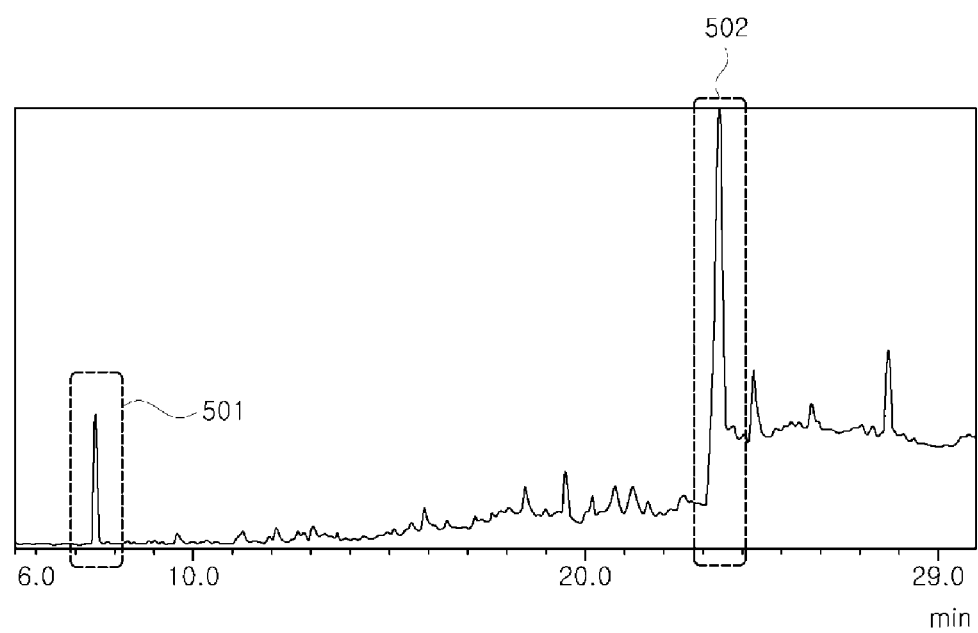
FIG. 5 is a view illustrating organic compound concentration peaks of a sap of a normal tree.
Figures 6, 7:
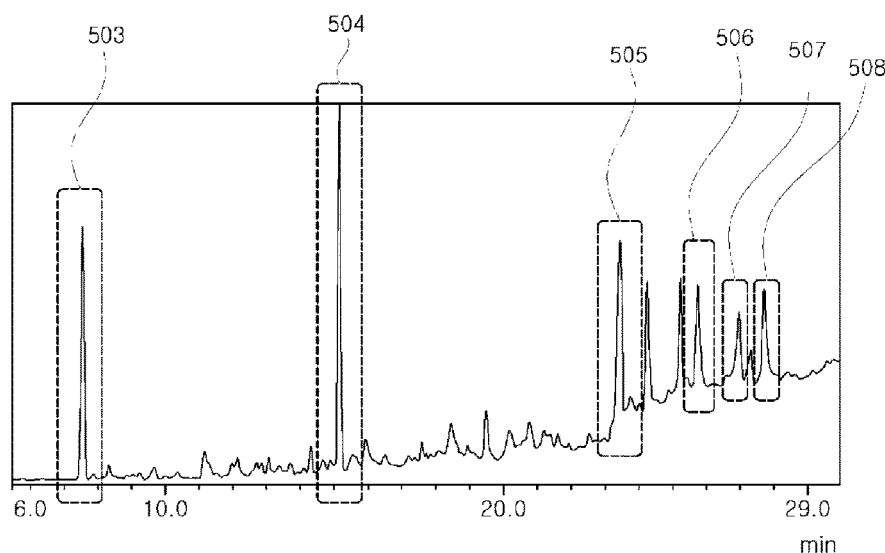
FIG. 6 is a table illustrating concentrations of organic compounds of FIG. 5 in detail.
FIG. 7 is a diagram illustrating organic compound concentration peaks of a sap of an infected tree.
Figure 10:
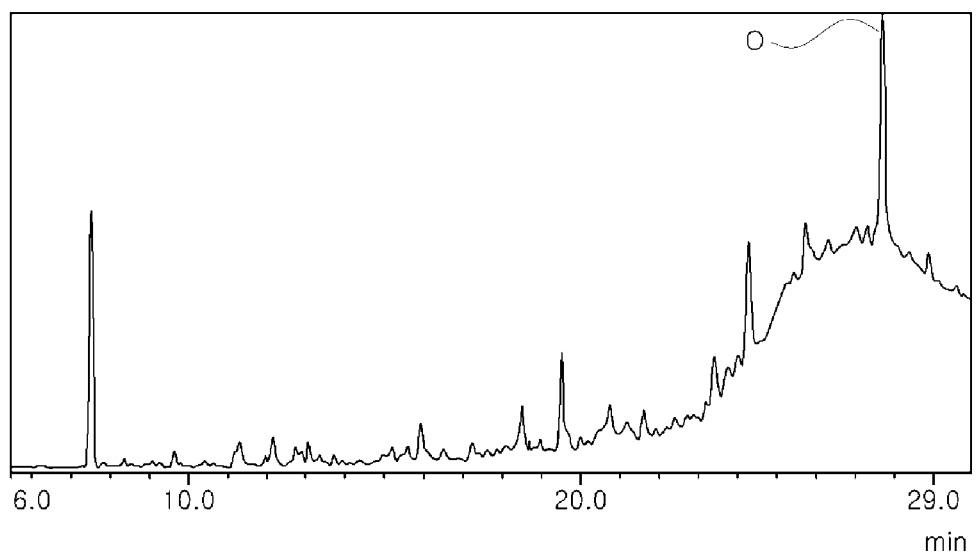

FIG. 5 is a view illustrating organic compound concentration peaks of a sap of a normal tree, FIG. 6 is a table illustrating concentrations of organic compounds of FIG. 5 in detail, FIG. 7 is a diagram illustrating organic compound concentration peaks of a sap of an infected tree, and FIG. 8 is a table illustrating concentrations of organic compounds of FIG. 7 in detail.

Meanwhile, referring to FIGS. 5 to 8, FIG. 5 is the organic compound concentration peak of sap of the normal tree and FIG. 7 is the organic compound concentration peak of sap of the infected tree. Referring FIGS. 5 and 7, it was shown that a concentration of (Z)-9-octadekenamide, which is the organic compound was significantly high in the infected tree of FIG. 7. Namely, it was shown that the sap of the pine infected with *Bursaphelenchus xylophilus* had a higher concentration of (Z)-9-octadekenamide than that of the sap of the normal tree.

As appears by this experiment, the sap of the normal tree and the sap of the infected tree showed different organic compound concentration peaks from each other. When the difference was standardized, the sap of the wild pine may be extracted and the extracted sap may be analyzed to rapidly determine whether the wild pine is infected with *Bursaphelenchus xylophilus* or not.

In this Experimental Example, the concentrations of the organic compounds contained in the saps of the normal tree and infected tree were measured by GC-MS, but the method of measuring the concentrations of the saps is not limited to the method using the GC-MS. That is, the measurement of the concentrations of the saps may be performed by mass spectrometry or concentration analysis in addition to the method using GC-MS. For example, an analytical method using a kit which measures color change or optical change by a chemical reaction with an indicator organic compound separated from a sap using a filter or chromatography may be applied.

Experimental Example 3: Sap Extraction from Wild Pine 100 g of fragments of wild pine chips were taken to determine whether the wild pine was infected with *Bursaphelenchus xylophilus* or not. The chips were washed to remove the foreign matter in the taken chips. After washing, the chips were dried in shade. Each dried fragment was immersed in the organic solvent for 1 hour at room temperature (25° C.). 200 g of hexane was used as the organic solvent. After immersion, 10 g of sap of the wild pine was obtained.

Experimental Example 4: Determination Whether Wild Fine is Infected with *Bursaphelenchus Xylophilus*

3 g of the sap of wild pine obtained in Experimental Example 2 was introduced into the Gas Chromatograph-Mass Spectrometer (GC-MS) to obtain a chart of the organic compound contained in the sap. Organic compound concentration peaks of the wild pine were shown in FIGS. 9 and 10.

First, referring to FIG. 9, it was found that the peak of junipene "J" was remarkable peak among the peaks of the organic compound of the sap of the wild pine. Namely, it was found that the concentration of junipene was remarkable concentration compared to that of the normal tree of Experimental Example 2. Therefore, the wild pine of this Experimental Example should be determined to be infected with *Bursaphelenchus xylophilus*.

In addition, referring to FIG. 10, it was found that a peak of (Z)-9-octadekenamide "O" in the peak of the organic compound of the sap of wild pine was remarkable peak. That is, it was found that the concentration of (Z)-9-octadekenamide was remarkable concentration compared to that of the normal tree of Experimental Example 2. Therefore, the wild pine of this Experimental Example should be determined to be infected with *Bursaphelenchus xylophilus*.

According to the inventive concept, the sap of the wild pine may be extracted and analyzed to rapidly determine whether the wild pine is infected with *Bursaphelenchus xylophilus* or not. *Bursaphelenchus xylophilus* may be early controlled through rapid determination to prevent pine necrosis.

FIG. 11 is an exemplary diagram illustrating deduction of an inspection distance depending on a concentration of an organic compound according to an embodiment of the inventive concept.

Following steps may be further included using embodiments of the inventive concept described above and data.

In an embodiment, when the first tree 110 is determined to be uninfected through the first determination, following steps may be further included.

Calculating a first inspection distance 310 based on a concentration of junipene or a concentration value of (Z)-9-octadekenamide, which are contained in the first concentration, immersing the second sample fragment taken from at least one second tree 120 located within the first inspection distance 310 to extract a second sap of the second tree 120 contained in the second sample fragment, analyzing a second concentration of an organic compound contained in the second sap, and secondarily comparing the second concentration with the reference concentration or the first concentration may be further included.

According to an embodiment of the inventive concept, inspection distances based on the concentration of junipene and the concentration value of (Z)-9-octadekenamide are stored in database of a determination server or device of whether or not infection of *Bursaphelenchus xylophilus*.

In another embodiment, the server or device may include a calculation module for calculating the inspection distance based on the concentration of junipene and the concentration value of (Z)-9-octadekenamide.

It is meant to calculate the first inspection distance 310 for selecting a tree to be additionally tested through the concentration of junipene and the concentration of (Z)-9-octadekenamide of the first tree 110, which is located in a specific area.

Then, when the concentration of junipene and the concentration of (Z)-9-octadekenamide contained in the second concentration are lower than the reference concentration or a critical ratio of the first concentration, a second determination may be further included to determine pines located within the first inspection distance 310 to be uninfected trees.

For example, referring to FIG. 11, when the first tree 110 is determined to be an uninfected tree, and the second tree 120 is determined to be an uninfected tree through the second determination, it is meant that the pines located within the first inspection distance 310 are determined to be uninfected trees.

Therefore, it is possible to determine whether the pines located within the first inspection distance 310 are infected with *Bursaphelenchus xylophilus* or not without collecting fragment samples of all pines and analyzing all fragment samples.

In addition, as an embodiment, when it is determined that the first tree 110 is an infected tree through the first determination, the following steps may be further included.

Calculating a second inspection distance 320 based on a concentration of junipene or a concentration value of (Z)-9-octadekenamide, which are contained in the first concentration, immersing a third sample fragment taken from at least one third tree 130 located within the second inspection distance 320 to extract a third sap of the third tree 130 contained in the third sample fragment, analyzing the third concentration of an organic compound contained in the third sap, and tertiary comparing the third concentration with the reference concentration or the first concentration may be further included.

It is meant to calculate the second inspection distance 320 for selecting a tree to be additionally tested through the concentration of junipene and the concentration of (Z)-9-octadekenamide of the first tree 110, which is located in a specific area.

Then, when the concentration of junipene and the concentration of (Z)-9-octadekenamide contained in the third concentration are higher than the concentration of junipene and the concentration of (Z)-9-octadekenamide contained in the reference concentration, a third determination may be further included to determine pines located within the second inspection distance 320 to be infected trees.

Figure 11:
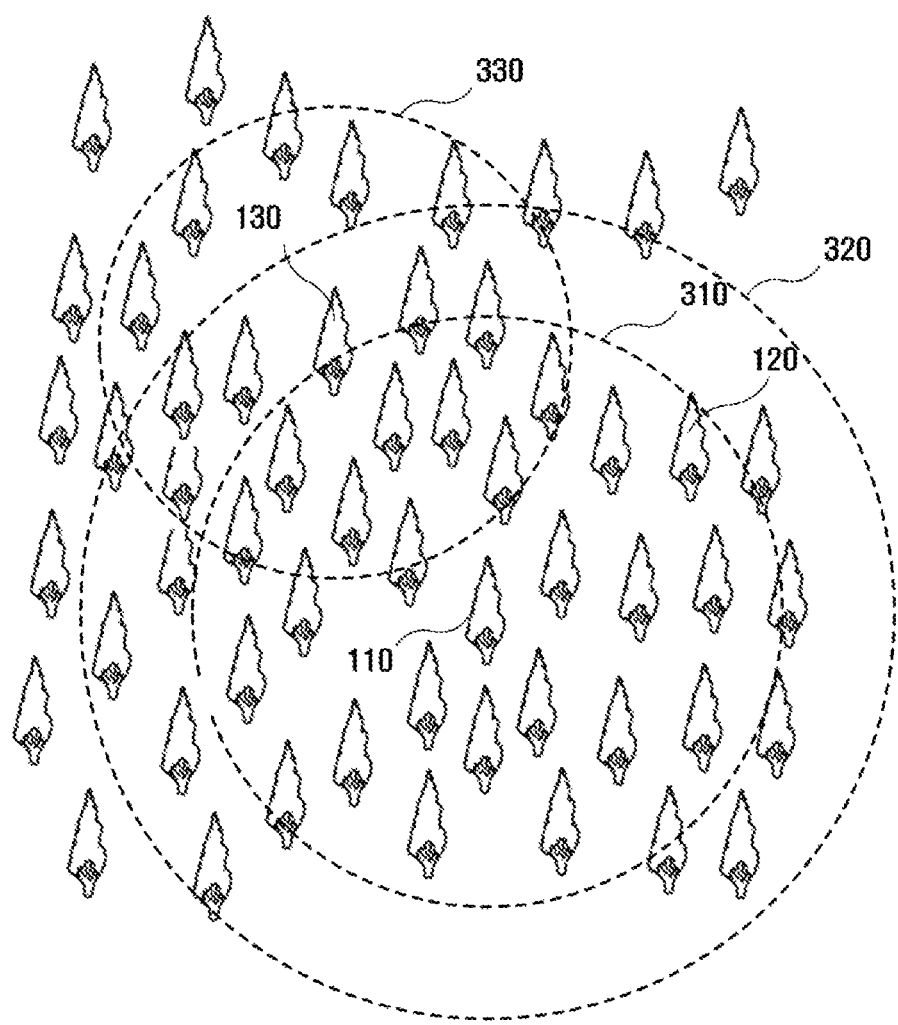
FIG. 11 is an exemplary diagram illustrating deduction of an inspection distance depending on a concentration of an organic compound according to an embodiment of the inventive concept.

Referring to FIG. 11, for example, when the first tree 110 is determined to be an infected tree and the third tree 130 is determined to be an infected tree through the third determination, it is meant that the pine located within the second inspection distance 320 are determined to be infected trees.

Therefore, it is possible to determine whether pines located within the second inspection distance 320 are infected with *Bursaphelenchus xylophilus* or not without collecting fragment samples of all pines and analyzing all fragment samples.

Here, when the concentration of junipene and the concentration of (Z)-9-octadekenamide contained in the third concentration are lower than the concentration of junipene and the concentration of (Z)-9-octadekenamide contained in the reference concentration, determining the third tree 130 as an uninfected tree and calculating the third inspection distance 330 from the third tree 130 based on the concentration of junipene and the concentration value of (Z)-9-octadekenamide contained in the third concentration may be further included.

As described above, when the first tree 110 is an infected tree and the third tree 130 is also an infected tree, all pines located within the second inspection distance 320 may be determined to be infected trees. However, when the third tree 130 is an uninfected tree, it may be not possible to determine which of the trees is started to be infected.

Therefore, when the first tree 110 is an infected tree and the third tree 130 is an uninfected tree in a result through the third determination, the third inspection distance 330 is calculated again through the concentration of junipene or the concentration of (Z)-9-octadekenamide, which are contained in third concentration based on the third tree 130.

Thereby, a user takes a fragment sample of tree located within the third inspection distance 330 based on the third tree 130 and performs sap extraction, concentration analysis, comparison, and determination to determine whether the associated tree is infected with *Bursaphelenchus xylophilus*.

Summarizing features and advantages of the inventive concept is as follows. That is, according to the inventive concept, the sap of the wild coniferous tree may be extracted and analyzed to rapidly determine whether the wild coniferous tree is infected with *Bursaphelenchus xylophilus* or not. The rapid determination may allow early control of the pine wilt disease, which prevents necrosis of the coniferous tree.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for determine whether a coniferous tree is infected with *Bursaphelenchus xylophilus* or not, the method comprising:
   performing a first sap extraction including immersing a first fragment sample taken from a first tree in a solvent and extracting a first sap of the first tree contained in the first fragment sample;
   performing a first analysis where a first concentration of an organic compound contained in the first sap is analyzed; and
   performing a first comparison where the first concentration is compared with a reference concentration of an organic compound contained in a sap of a tree uninfected with *Bursaphelenchus xylophilus*.

2. The method of claim 1, wherein the performing of the first sap extraction includes immersing the first fragment sample in the solvent for 0.5 to 2 hours, and a mixture ratio of the first fragment sample and the solvent is 1:1 to 1:3 by mass.

3. The method of claim 1, wherein the solvent is selected from one or more of acetone, ethyl acetate, diethyl ether, glycerin, ethylene glycol, propylene glycol, butylene glycol, benzene, chloroform, hexane, and alcohol having 1 to 4 carbon atoms.

4. The method of claim 1, further comprising:
   determining whether the first tree is infected with *Bursaphelenchus xylophilus* or not depending on a result of the performing of the first comparison,
   wherein, when at least one of a first condition where a concentration of junipene contained in the first concentration is higher than a concentration of junipene contained in the reference concentration or a second condition where a concentration of (Z)-9-octadekenamide contained in the first concentration is higher than a concentration of (Z)-9-octadekenamide contained in the reference concentration is satisfied, the first tree is determined to be an infected tree.

5. The method of claim 4, further comprising:
   calculating a second inspection distance based on the concentration of junipene or a concentration value of (Z)-9-octadekenamide contained in the first concentration when the first tree is determined to be an infected tree;
   performing a third sap extraction including immersing a third fragment sample taken from at least one third tree located within the second inspection distance in the solvent and extracting a third sap of the third tree contained in the third fragment sample;
   performing a third analysis where a third concentration of an organic compound contained in the third sap is analyzed; and
   performing a third comparison where the third concentration is compared with the reference concentration or the first concentration.

6. The method of claim 5, further comprising:
   performing a third determination where pines located within the second inspection distance are determined to be infected trees when a concentration of junipene or a concentration of (Z)-9-octadekenamide contained in the third concentration is higher than the reference concentration.

7. The method of claim 5, further comprising:
   determining the third tree as an uninfected tree when the concentration of junipene contained or the concentration value of (Z)-9-octadekenamide contained in the third concentration is lower than the concentration of junipene or the concentration of (Z)-9-octadekenamide contained in the reference concentration; and
   calculating a third inspection distance from the third tree based on the concentration of junipene contained in the third concentration or the concentration value of (Z)-9-octadekenamide contained in the third concentration.

8. The method of claim 4, further comprising:
performing a fourth sap extraction including immersing a fourth fragment sample taken from the first tree after a specific time from when the first fragment is taken, when the first tree is determined to be an uninfected tree in the first determination and extracting a fourth sap of the first tree contained in the fourth fragment sample;
performing a fourth analysis where the fourth concentration of an organic compound of the fourth sap is analyzed; and
setting the first tree to a protective monitoring tree when at least one of the concentration of junipene or the concentration of (Z)-9-octadekenamide contained in the fourth concentration rises more than the critical ratio of the concentration contained in the first concentration.

9. The method of claim 5, wherein the pine is any one of Japanese larch (*Larix kaempferi*), spruce (*Picea jezoensis*), needle fir (*Abies holophylla*), Himalayan cedar (*Cedrus deodara*).

10. The method of claim 4, further comprising:
calculating a first inspection distance based on the concentration of junipene or a concentration value of (Z)-9-octadekenamide contained in the first concentration when the first tree is determined to be an uninfected tree;
performing a second sap extraction including immersing a second fragment sample taken from at least one second tree located within the first inspection distance and extracting a second sap of the second tree contained in the second fragment sample;
performing a second analysis where a second concentration of an organic compound contained in the second sap is analyzed; and
performing a second comparison where the second concentration is compared with the reference concentration or the first concentration.

11. The method of claim 10, further comprising:
performing a second determination where pines located within the first inspection distance are determined to be uninfected tree when a concentration of junipene or a concentration of (Z)-9-octadekenamide contained in the second concentration is lower than the concentration of junipene or the concentration of (Z)-9-octadekenamide contained in the reference concentration or when the concentration of junipene or the concentration of (Z)-9-octadekenamide contained in the second concentration is lower than a critical ratio of the first concentration.

12. The method of claim 1, further comprising:
introducing the extracted sap into a gas chromatograph mass spectrometer and obtaining a chart containing an organic compound of the sap.

13. The method of claim 1, wherein the coniferous tree is any one of pine (*Pinus densiflora*), Korean pine (*Pinus koraiensis*), black pine (*Pinus thunbergii*), Japanese white pine (*Pinus parviflora*), white pine (*Pinus strobus*), pitch pine (*Pinus rigida*).

* * * * *